(12) United States Patent
Anderson et al.

(10) Patent No.: US 9,301,824 B2
(45) Date of Patent: Apr. 5, 2016

(54) HYDRAULIC URETHRAL OCCLUSIVE DEVICE

(71) Applicant: GT UROLOGICAL, LLC, Minneapolis, MN (US)

(72) Inventors: David W. Anderson, Brooklyn Park, MN (US); Bernard J. Esarey, Vermilion, OH (US)

(73) Assignee: GT Urological, LLC, Minneapolis, MN (US)

( * ) Notice: Subject to any disclaimer, the term of this patent is extended or adjusted under 35 U.S.C. 154(b) by 145 days.

(21) Appl. No.: 13/863,459

(22) Filed: Apr. 16, 2013

(65) Prior Publication Data

US 2013/0274546 A1  Oct. 17, 2013

Related U.S. Application Data

(60) Provisional application No. 61/686,902, filed on Apr. 16, 2012.

(51) Int. Cl.
*A61F 2/04* (2013.01)
*A61F 2/00* (2006.01)

(52) U.S. Cl.
CPC ..................................... *A61F 2/004* (2013.01)

(58) Field of Classification Search
CPC ... A61F 2/0004; A61F 2/0022; A61F 2/0027; A61F 2/0031; A61F 2/004; A61F 2002/75; A61F 2002/745; A61F 2250/0003; A61F 2250/0013
USPC ........................................................... 600/31
See application file for complete search history.

(56) References Cited

U.S. PATENT DOCUMENTS 3,863,622 A    2/1975  Buuck
3,903,894 A    9/1975  Rosen et al.
(Continued)

FOREIGN PATENT DOCUMENTS

CN    1303253      7/2001
CN    201356677    12/2009
(Continued)

OTHER PUBLICATIONS

International Search Report for PCT/US2013/036691 mailed Aug. 19, 2013, 3 pages.
(Continued)

*Primary Examiner* — Charles A Marmor, II
*Assistant Examiner* — Thaddeus Cox
(74) *Attorney, Agent, or Firm* — Hamre, Schumann, Mueller & Larson, P.C.

(57) ABSTRACT

A totally implantable method for occluding the urethra or bladder neck utilizing an occlusive cuff connected to a control mechanism via a conduit tube. The occlusive cuff is reversibly changed from an activated (occlusive condition) to a de-activated (non-occlusive) condition by depressing a deactivation button contained within a resilient, elastomeric sheath surrounding the control mechanism. The occlusive condition is once again obtained by depressing an activation button also situated within the resilient sheath. In the occlusive condition, a preset tension is applied to a flexible diaphragm through a tensioning suture by a constant force spring contained within the control mechanism. This tension is translated into an occlusive pressure applied to the urethra or bladder neck sufficient to prevent urinary leakage.

17 Claims, 7 Drawing Sheets

(56) References Cited

U.S. PATENT DOCUMENTS

| | | |
|---|---|---|
| 4,118,805 A | 10/1978 | Reimels |
| 4,222,377 A | 9/1980 | Burton |
| 4,412,530 A | 11/1983 | Burton |
| 4,417,567 A * | 11/1983 | Trick ............... 600/31 |
| 4,419,985 A * | 12/1983 | Trick ............... 600/31 |
| 4,632,114 A * | 12/1986 | Todd et al. ........ 600/31 |
| 4,682,583 A | 7/1987 | Burton et al. |
| 4,878,889 A | 11/1989 | Polyak |
| 4,938,760 A | 7/1990 | Burton et al. |
| 4,994,020 A * | 2/1991 | Polyak ............. 600/31 |
| 5,509,888 A | 4/1996 | Miller |
| 5,518,504 A | 5/1996 | Polyak |
| 5,704,893 A | 1/1998 | Timm |
| 5,888,188 A | 3/1999 | Srougi et al. |
| 6,074,341 A | 6/2000 | Anderson et al. |
| 6,117,067 A | 9/2000 | Gil-Vernet |
| 6,463,935 B1 | 10/2002 | Forsell |
| 6,709,385 B2 | 3/2004 | Forsell |
| 7,060,080 B2 | 6/2006 | Bachmann |
| 8,007,429 B2 | 8/2011 | Anderson et al. |
| 2002/0111530 A1 | 8/2002 | Bakane |
| 2004/0147886 A1 * | 7/2004 | Bonni ............... 604/327 |
| 2006/0264697 A1 | 11/2006 | Timm et al. |
| 2009/0012351 A1 * | 1/2009 | Anderson et al. ... 600/30 |
| 2010/0160716 A1 * | 6/2010 | Snow .................. 600/31 |
| 2010/0211175 A1 | 8/2010 | Gomez-Llorens |
| 2010/0331825 A1 | 12/2010 | Hakky et al. |
| 2015/0045609 A1 * | 2/2015 | Anderson ......... A61F 2/004 600/31 |

FOREIGN PATENT DOCUMENTS

| | | |
|---|---|---|
| EP | 202815 | 11/1986 |
| FR | 2922754 | 5/2009 |
| WO | 2009094431 | 7/2009 |

OTHER PUBLICATIONS

Written Opinion for PCT/US2013/036691 mailed Aug. 19, 2013, 6 pages.

Office Action issued for corresponding Chinese patent application No. 201380020026.6, dated Sep. 30, 2015 (28 pages, including English translation).

Extended European Search Report for European application no. 13778864.2, dated Dec. 21, 2015 (7 pages).

* cited by examiner

HYDRAULIC URETHRAL OCCLUSIVE DEVICE

This invention was made with government support under SBIR Grant Number R43 DK092007-01 awarded by the National Institutes of Health. The government has certain rights in the invention.

FIELD

The disclosure herein relates to embodiments of a hydraulic urethral occlusive devices (HUOD) that are entirely inserted or surgically implanted within the body for controlling the lack of urinary or bowel restraint. These devices are commonly referred to as "artificial sphincters" which are installed within the body to aid or replace the body's natural sphincter.

BACKGROUND

One such device by American Medical Systems, Inc. is the AUS 800, which is a totally implantable hydraulic sphincter implanted in both males and females experiencing urinary incontinence and has been on the market for over 35 years. The AUS 800 and its predecessors are described in U.S. Pat. Nos. 3,863,622; 4,222,377; 4,412,530; and 4,878,889. The AUS 800 consists of a silicone pressure regulating balloon implanted in the prevesical space, a silicone control pump implanted in the scrotum or labia, and a silicone urethral occlusive cuff wrapped around the bulbous urethra in males or bladder neck in females. Each component is filled with saline or radiopaque contrast media. Tubing, emanating from each component, is routed between incisions and appropriate connections are made. The device is deactivated for a period of approximately 6 weeks to allow tissue healing to proceed and urethral edema to subside. At activation, the control pump is squeezed sharply to unseat a poppet and open operational fluid flow paths. The patient is taught to operate the device by squeezing the control pump through the scrotal or labial skin. This action transfers fluid from the cuff to the pressure regulating balloon. The balloon forces the fluid through a fluid restrictor and back into cuff to reestablish an occlusive urethral pressure within 3-5 minutes. The AUS 800 is complicated to implant, is prone to fluid leakage, and causes urethral atrophy and erosion. Despite these draw backs, the AMS 800 is the only commercially available artificial urinary sphincter.

Another such type of mechanical artificial urinary sphincter, the Timm-AUS, is described in U.S. Pat. Nos. 5,704,893 and 6,074,341, both of which are entitled VESSEL OCCLUSIVE APPARATUS AND METHOD. The Timm-AUS is a one piece device not requiring saline filling or intra-operative assembly. Depression of a deactivation button through the scrotal skin causes a urethral occlusive sheath to expand and remove occlusive pressure from the urethra to allow normal urination. Depression of an activation button allows the occlusive sheath to contract and reapply urethral pressure to prevent urethral leakage. Human implantation experience with the Timm-AUS was hindered by formation of a tough, fibrous capsule surrounding the device which prevented expansion of the Occlusive Sheath.

Another mechanical method of occluding the urethra is demonstrated by U.S. Pat. No. 8,007,429 A1 entitled VESSEL OCCLUSIVE DEVICE AND METHOD FOR OCCLUDING A VESSEL. In this patent, depression of an activation button allows a constant force spring to apply tension to a compressible tape wrapped circumferentially about the urethra. In so doing, urinary leakage is prevented. Depressing a deactivation button removes spring tension and urethral compression to allow unobstructed urinary voiding.

A hybrid mechanical/hydraulic artificial urethral sphincter is described in US patent application publication 2010/0211175 A1 SURGICAL IMPLANT, IN PARTICULAR ARTIFICIAL SPHINCTER WITH ADJUSTED PRESSURE. This patent application publication describes a helical spring biased piston which maintains hydraulic pressure within an inflatable cuff circumferentially disposed about the urethral circumference. Depression of a secondary hydraulic bladder forces fluid from the piston into a third holding bladder to remove hydraulic pressure from the urethra. The pressurized fluid within this third bladder is then slowly discharged back into the piston through a fluid restrictor to re-establish hydraulic pressure about the urethra. Pressurized fluid may be locked out of the hydraulic cuff to remove pressure for a prolonged period as might be required immediately following implantation and during sleep when urinary leakage is not as problematic. Lockout is accomplished by depressing a lockout button. Returning the device to its normal function is accomplished by depressing the lockout button on its opposite side.

As evidenced by clinical experience with the above devices, it is difficult to teach the patient to identify and then operate the small lockout valve which is encased within and masked by scrotal tissues. Additionally, cuff refilling through the fluid restrictor takes 3 to 5 minutes. This allows ample time for the patient to believe that his bladder is empty and leave the commode. Residual urine within the bladder may then leak through the uncompressed urethra to wet the patient's clothing.

SUMMARY

A hydraulic urethral occlusive device (HUOD) is described herein that is an implantable artificial urinary sphincter intended to provide the incontinent patient protection against urine leakage and "at will" control over his/her voiding function. The HUOD is intended to address the drawbacks of the state of the art by providing several features described herein and illustrated in the drawings.

DRAWINGS

These and other features, aspects, and advantages of the hydraulic urethral occlusive device will become better understood when the following detailed description is read with reference to the accompanying drawing, wherein.

Figure 1:
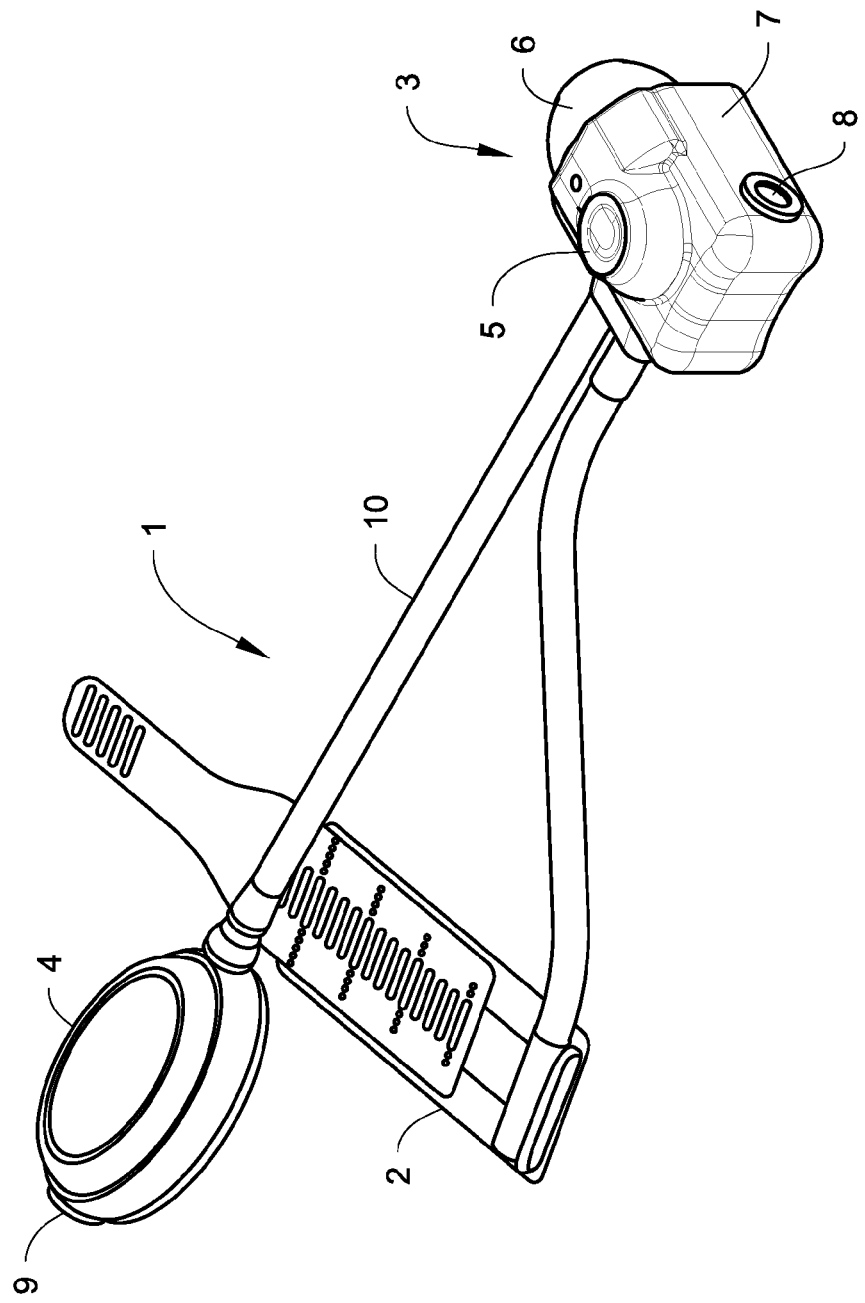
FIG. 1 is a perspective view of a hydraulic urethral occlusive device according to one embodiment, and shown with one embodiment of an occlusive cuff not encircling a urethra.
Figure 5A:
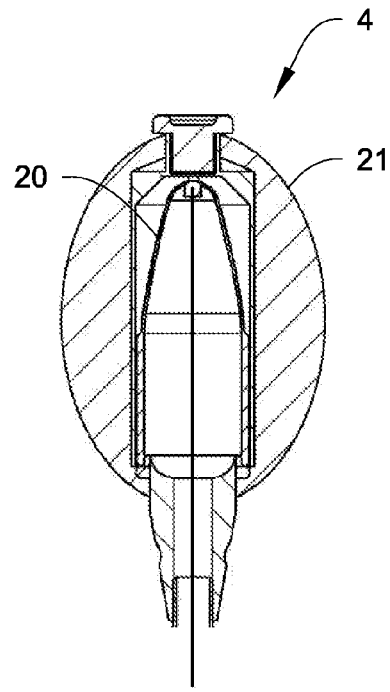
Figure 5B:
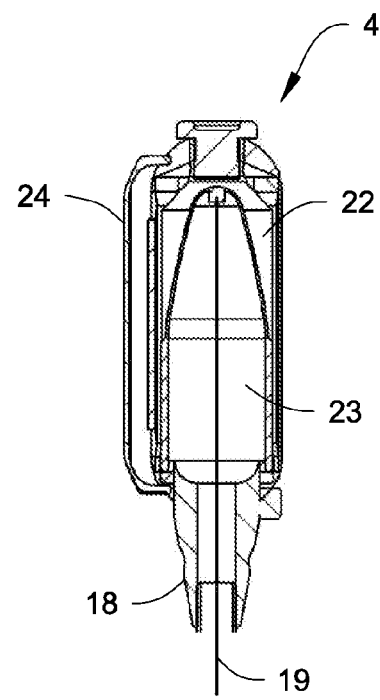
Figure 5C:
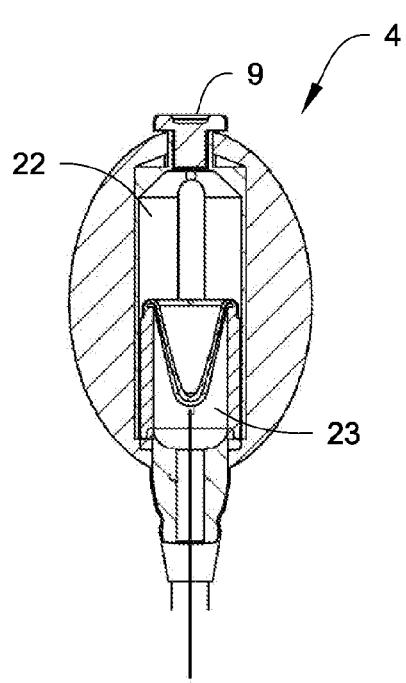
Figure 5D:
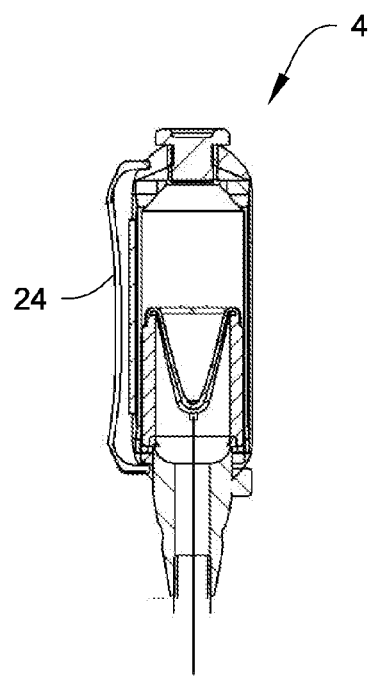

FIG. 5A is frontal sectional view of a pressure compensator of the hydraulic urethral occlusive device of FIG. 1, according to one embodiment, and shown in a state when the hydraulic urethral occlusive device is off, unpressurized. FIG. 5B is a lateral sectional view of the pressure compensator of FIG. 5A in the state when the hydraulic urethral occlusive device is off, unpressurized. FIG. 5C is frontal sectional view of the pressure compensator of FIG. 5A, and shown in a state when the device is on, pressurized. FIG. 5D is a lateral sectional view of the pressure compensator of FIG. 5A in the state when the hydraulic urethral occlusive device is on, pressurized.

Figure 6A:
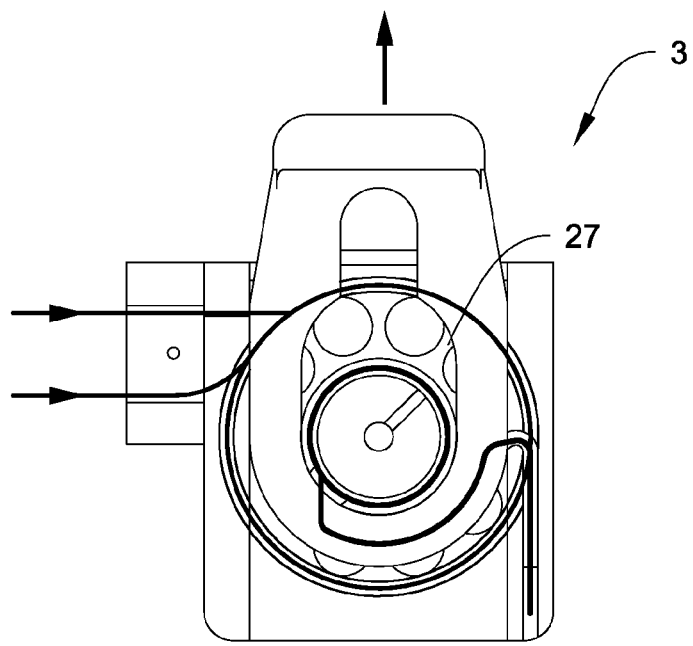
Figure 6B:
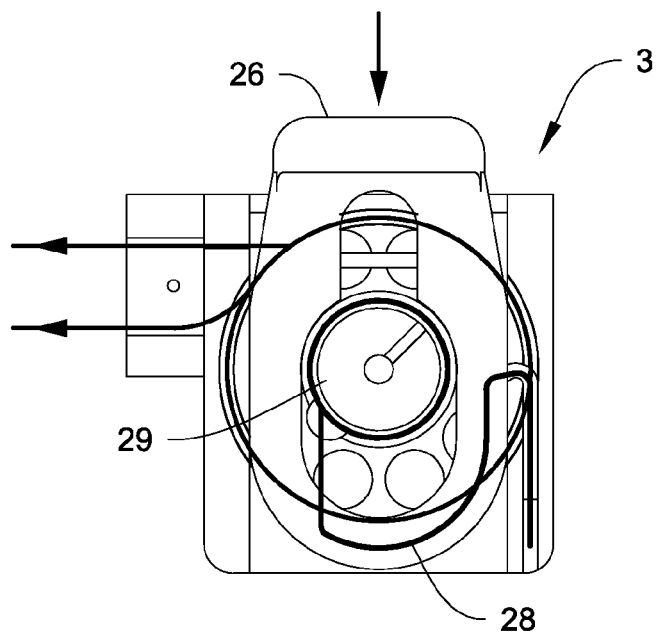

FIG. 6A is a side view of a control mechanism of the hydraulic urethral occlusive device of FIG. 1, according to one embodiment, and shown in a state when the hydraulic urethral occlusive device is activated. FIG. 6B is another side view of the control mechanism of the hydraulic urethral occlusive device of FIG. 6A, and shown in a state when the hydraulic urethral occlusive device is deactivated.

Figure 7A:
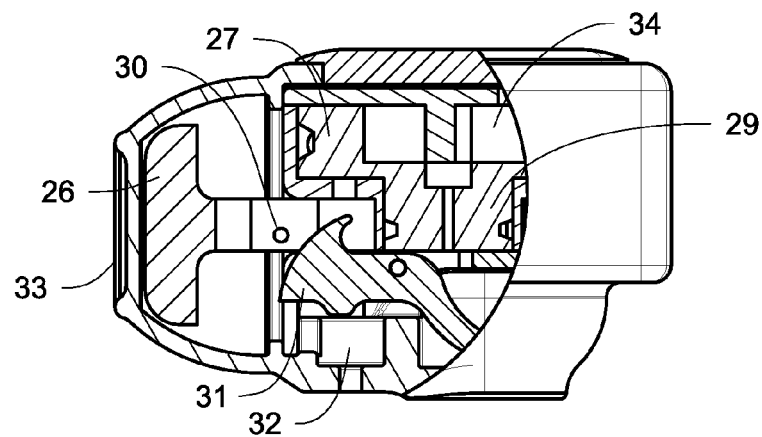
Figure 7B:
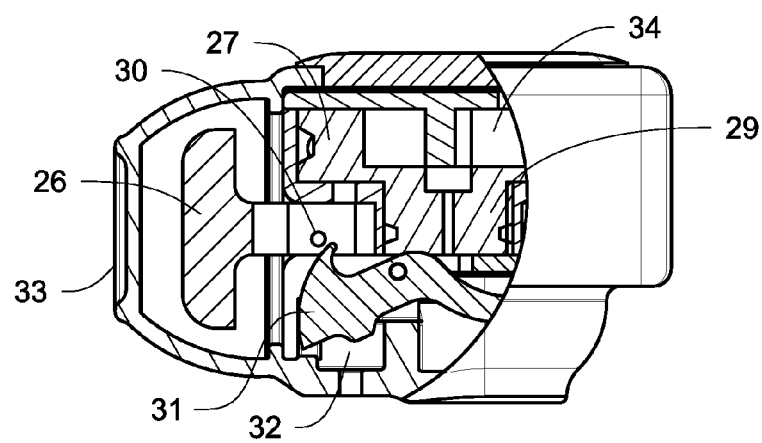
Figure 7C:
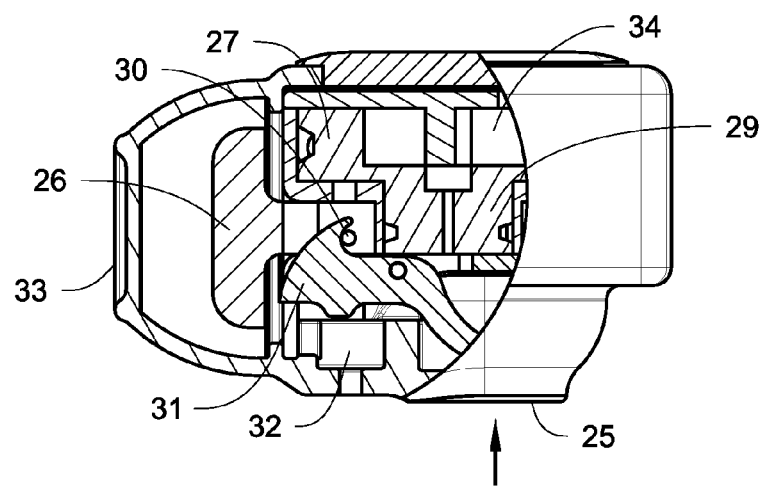

FIG. 7A is a side sectional view of the control mechanism of FIG. 6A, shown in the activated state. FIG. 7B is a side sectional view of the control mechanism of FIG. 6A, shown moving to the deactivated state. FIG. 7C is a side sectional view of the control mechanism of FIG. 6A, shown in the deactivated state.

Figure 8:
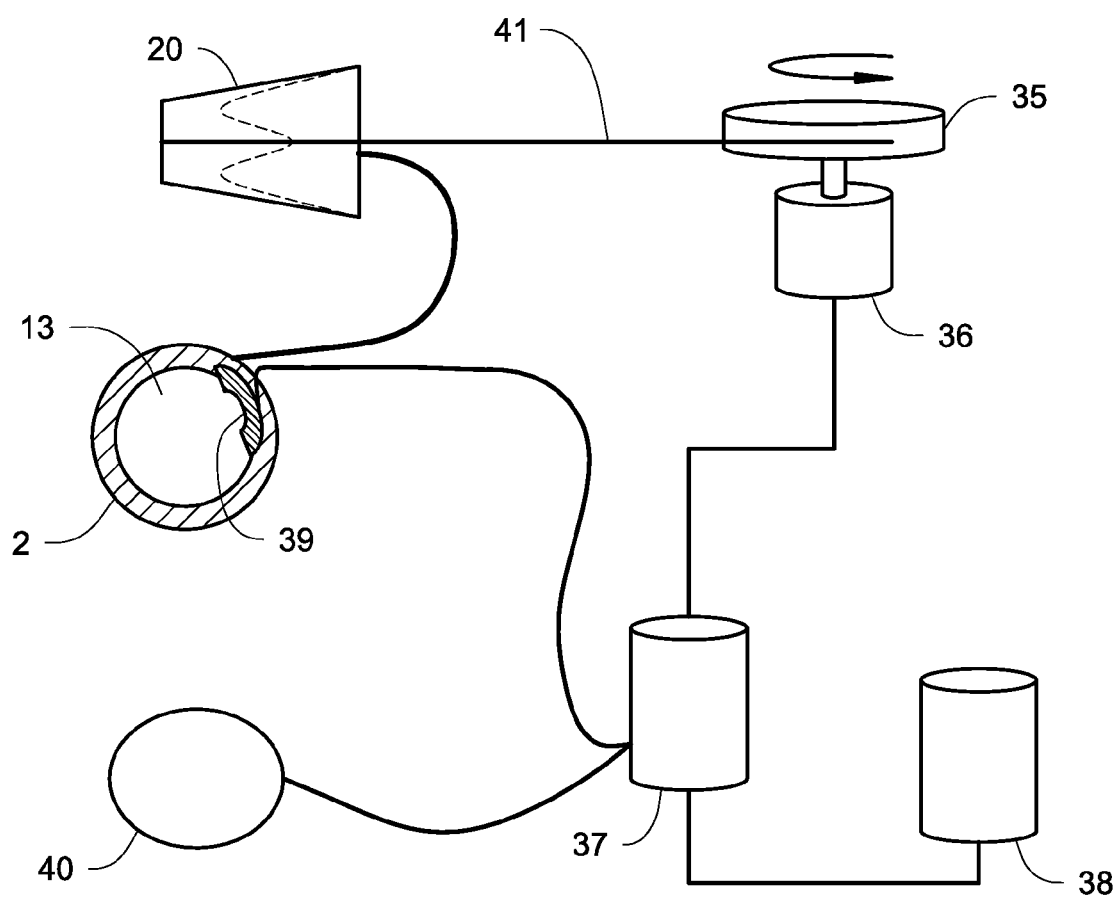

FIG. 8 is diagrammatic view of a hydraulic urethral occlusive device, according to another embodiment, in which the control mechanism is an electro-mechanical control mechanism While the above-identified figures set forth particular embodiments of the hydraulic urethral occlusive device, other embodiments are also contemplated, as noted in the discussion. In all cases, this disclosure presents illustrated embodiments of the hydraulic urethral occlusive device by way of representation but not limitation. Numerous other modifications and embodiments can be devised by those skilled in the art which fall within the scope and spirit of the principles of the heat recovery systems and methods described herein.

DETAILED DESCRIPTION

A hydraulic urethral occlusive device (HUOD) 1, as depicted for implantation in males is illustrated in FIG. 1. The hydraulic urethral occlusive device is a one-piece device implanted through a single perineal or peno-scrotal incision. An inflatable hydraulic occlusive cuff 2 encircles the urethra and is permanently attached via a flexible tube to the control mechanism 3 implanted in the scrotum. A pressure compensator 4 is likewise permanently attached to the control mechanism 3 via a flexible conduit 10 to allow placement in the subcutaneous tissues of the abdomen, thigh or alternately in the pre-vesical space. The occlusive cuff 2 is implanted in an uninflated, deactivated condition for approximately 6 weeks post-operatively to facilitate healing and allow pain and edema to subside. Following this deactivation period, the urologist activates the device by depressing an activation button 5 through the intact scrotal skin. In so doing, the occlusive cuff 2 inflates to apply a preset occlusive pressure within the range of 60-80 cm $H_2O$ to the urethra. The patient is then free to depress a deactivation button 6 to evacuate hydraulic fluid from the occlusive cuff 2 and allow unobstructed voiding. To re-establish urethral occlusive pressure and continence, the patient pushes the activation button 5.

The control mechanism 3 is encapsulated by a silicone boot 7 which incorporates a needle port or septum 8. All other HUOD components likewise can be encapsulated by silicone rubber coverings to prevent hydraulic solution leakage and the incursion of bodily fluids. The control mechanism 3 is in fluid communication with the occlusive cuff 2 and the inner portion of the pressure compensator 4. The inner portion of the pressure compensator 4 is further surrounded by an outer pressure capacitor chamber containing a second and separate fluid volume. This chamber also incorporates a needle puncture port or septum 9. Each separate fluid volume defined by the above-mentioned structures may be filled by accessing each septum 8 and 9 with a hypodermic needle and infusing appropriate filling solutions. The pressure compensator 4 and control mechanism 3 are joined by the flexible conduit 10.

The first fluid volume contained within the control mechanism 3, occlusive cuff 2, and the inner portion of the pressure compensator 4 is filled with normal saline or radiopaque solutions intended to allow visualization of these otherwise, non-radiopaque structures. The outer pressure capacitor chamber is filled with normal saline only, so as not to obscure radiographic visualization of the inner portion of the pressure compensator 4.

The occlusive cuff 2 may be adjusted to accommodate varying urethral circumferences as might be found in the human population. The urethral circumference may first be measured with a flexible measuring tape. The cuff 2 is then wrapped around the urethra and locked into a detent corresponding to the measured urethral circumference.

The hydraulic urethral occlusive device is also configurable for female implantation through a transvaginal or abdominal incision. In this case, the occlusive cuff 2 would encircle the bladder neck or mid-urethra. The control mechanism 3 for female implantation would be miniaturized for implantation in the labia or abdominal skin where it could be operated by manual depression activation and deactivation buttons 5, 6, through the labial or abdominal tissue. The pressure compensator 4 may be implanted in similar locations described for male implantation. The control mechanism 3 may also be replaced with a motor driven servo which would alternately apply or remove tension from the pressure compensator causing it to apply or remove pressure from the cuff 2 (see e.g. embodiment of FIG. 8 further described below). The addition of implantable pressure transducing elements and a closed-loop control system would allow this device to respond in real-time to increases in bladder and, or intra-abdominal pressures which may cause the patient to leak urine (see e.g. embodiment of FIG. 8 further described below).

Advantages over the current state of the art can include, for example:

no intra-operative assembly required;

no tubing connectors which are prone to disconnection;

allows post-implantation re-pressurization to allow degree of continence to be incrementally improved;

single incision implantation with reduced surgical morbidity;

a "one size fits all" cuff design which eliminates the need for a hospital to stock devices in a multitude of sizes which are then selected at the time of surgery;

greatly reduced operative time as evidenced by human implants with predecessor device;

large buttons which are easily identifiable and operable by both physician and patient without the need for a separate deactivation button; and no time delay when changed from the deactivated to activated conditions to reduce unexpected urinary leakage.

The hydraulic urethral occlusive device also has applications in the areas of fecal incontinence, gastro-esophageal reflux disease (GERD), and gastric banding for weight loss. Other disease states which may be served by occlusion or support of tubular body passages may lend further usage to the HUOD concept.

As described above, the hydraulic urethral occlusive device is a totally implantable artificial urinary sphincter intended to prevent urinary leakage in both males and females. Men frequently become incontinent of urine following surgeries to remove cancerous prostates. Women are often rendered incontinent due to the pelvic trauma caused during childbirth and due to a laxity of the pelvic muscles occurring due to aging. To a lesser degree, men and women are rendered incontinent due to trauma, infection and birth defects. The American Medical Systems, Inc. AUS 800 is the only commercially available, totally implantable artificial urinary sphincter. The complexity of its implantation is due to the requirement to intra-operatively fill and assemble its three components. The AUS 800 often fails due wear in its componentry which leads to fluid leakage and post-operative infections. Urethral atrophy and erosion sometimes occur and are suspected to be due to the crenate shape of its occlusive cuff The AUS 800 is available with a number of occlusive pressure ranges with 61-70 cm $H_2O$ being the pressure most frequently selected.

Referring back to FIG. 1, the hydraulic urethral occlusive device 1 is a one-pieced device not requiring assembly. The hydraulic urethral occlusive device 1 may be filled with saline solution, or a combination of saline solution and radiopaque dyes intended to aid in visualization of anatomical placement and functionality. The hydraulic urethral occlusive device has the occlusive cuff 2 to surround the urethra or bladder neck and has the control mechanism 3, which is implanted in the scrotum in males and the labia or abdominal wall in females. The pressure compensator 4 is joined to the control mechanism 3 by the conduit 10 through which tensioning cables pass (see e.g. FIGS. 5A through 5D). The conduit 10 is flexible to accommodate bodily movement by the human implant subject.

Occlusive Cuff

Figure 2:
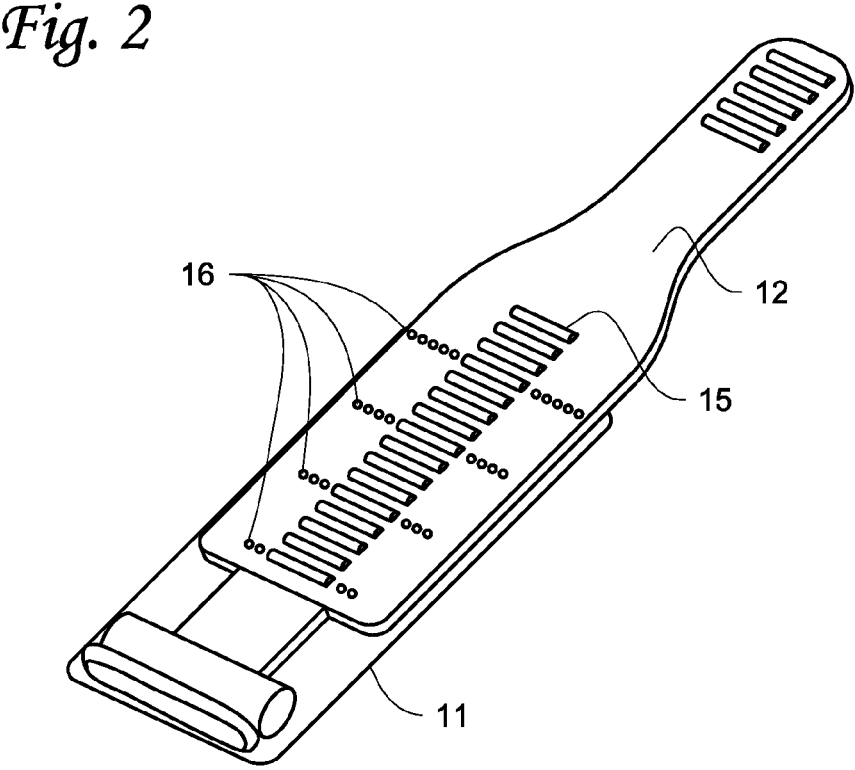
FIG. 2 is a perspective view of the occlusive cuff alone from the hydraulic urethral occlusive device of FIG. 1, shown in a flat condition.
Figure 3:
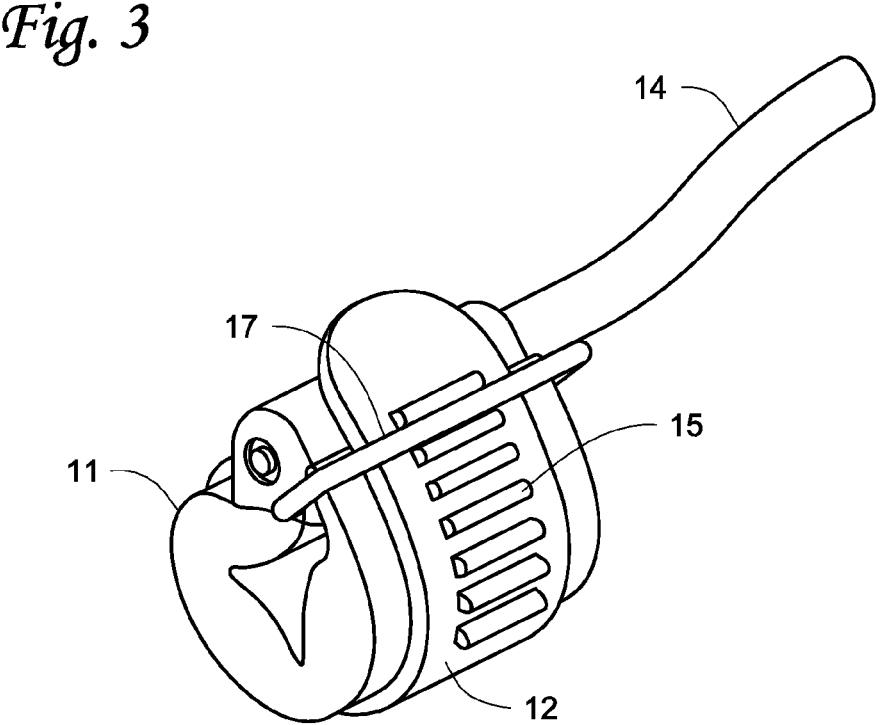
FIG. 3 is perspective view of the occlusive cuff alone from the hydraulic urethral occlusive device of FIG. 1, shown encircling a urethra.
Figure 4A:
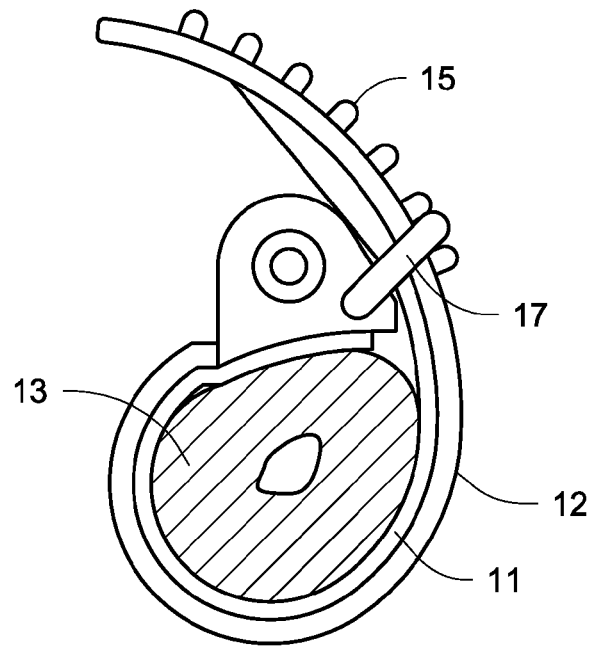
FIG. 4A is a side view of the occlusive cuff of alone from hydraulic urethral occlusive device of FIG. 1, shown sized around a relatively smaller urethra.
Figure 4B:
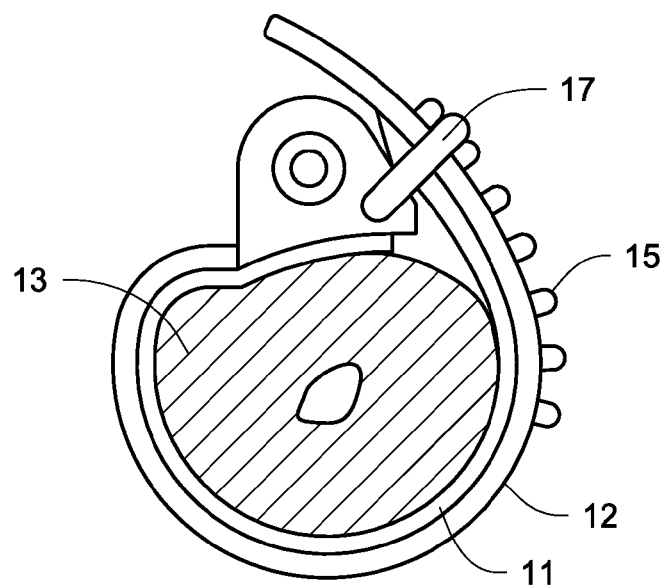
FIG. 4B is a side view of the occlusive cuff of alone from hydraulic urethral occlusive device of FIG. 1, shown sized around a relatively larger urethra.

Further details of the occlusive cuff 2 are shown in FIGS. 2-4. FIG. 2 shows the occlusive cuff 2 in its flat condition prior to implantation and in its condition when it could encircle a urethra 13 in FIGS. 3 and 4. The occlusive cuff has a thin-walled, expandable pouch 11 to which is affixed a semi-flexible cuff backing strip 12 as shown in FIG. 2. When encircling the urethra 13 (see e.g. FIGS. 4A and 4B), the fluid-tight expandable pouch 11 may be alternately expanded or deflated by infusion of a suitable filling media such as isotonic saline or radiopaque contrast media. Inflation occurs through a flexible input tube 14, such as indicated in FIG. 3. The occlusive cuff 2 with the expandable pouch 11 inflated is also shown in FIG. 3. When the expandable pouch 11 is inflated, the pressure exerted on the urethra 13 is sufficient to prevent or minimize urinary leakage. Historical clinical evidence suggests that this pressure should be in the range of 60-80 cm $H_2O$ to provide adequate leak resistance without causing undue urethral atrophy or tissue erosion. When the expandable pouch 11 is deflated, pressure is removed from the urethra 13 to allow normal, unobstructed urinary drainage. The cuff backing strip 12 is positioned on the expandable pouch 11 surface away from the urethral surface and acts to maximize urethral occlusion efficiency by minimizing radial expansion of the expandable pouch 11 away from the urethra 13. Sizing Detents 15 are positioned on the cuff backing strip 12 to allow the occlusive cuff 2 to be sized to accommodate anatomical variations in urethral circumferences as may occur in the human population as shown in FIGS. 4B and 4B. Clinical experience indicates that the range of urethral circumferences in the human male population ranges from 3.5 cm to 5.0 cm. Sizing indicators 16 may be associated with the detents 15 to provide the surgeon with urethral circumference information. When the occlusive cuff 2 is surgically wrapped around the urethra 13, the free end of the occlusive cuff 2 is inserted through a locking clip 17 and advanced to the detent 15 to provide a close fit between the occlusive cuff 2 and urethra 13.

The expandable pouch 11 may be constructed using an inner substrate of expanded polytetrafluoroethylene (ePTFE). The substrate may be in tubular form, sealed at either end to form a leak-proof pouch. The flat width of the tubular expandable pouch 11 may be within the range of 1 cm to 3 cm and ePTFE materials with a wall thickness of 0.003"-0.005" and an internodal distance (porosity) of 30μ-50μ have been shown to have an appropriate flexibility. The substrate is rendered leak-proof by application of a thin coat of silicone rubber applied by a dispersion dip molding process. The ePTFE porosity range indicated above, allows deposition of silicone dispersion into the porous interstices to create a bond between the silicone outer layer and the ePTFE substrate. Wear and subsequent filling media leakage is minimized by applying low coefficient of friction coatings to the opposing outer silicone surfaces. These coatings include polytetrafluoroethylene (PTFE) particulate over-sprays or NuSil MED 6670 or NuSil MED 6671 silicone dispersions. Wear created by relative movement of opposing surfaces on the inner of the expandable pouch 11 surfaces is minimized by the low coefficient of friction nature of the ePTFE substrate.

Alternately, the expandable pouch 11 may be entirely manufactured from silicone using a dispersion casting or molding method. To reduce the tendency of wear induced holes in the expandable pouch 11, polytetrafluoroethylene (PTFE) particulate over-sprays or NuSil MED 6670 or NuSil MED 6671 silicone dispersions may be used as coatings on the inner and outer surfaces of the expandable pouch 11.

Pressure Compensator

In FIGS. 5A to 5D, the pressure compensator 4 is a structure attached to the control mechanism 3 via a flexible conduit tube 18, 10. A tension cord 19 travels from the control mechanism 3 through the conduit tube 18 to the apex of the pressure compensator diaphragm 20. The pressure compensator diaphragm 20 is a thin-walled, bullet-shaped diaphragm which operates between an expanded and collapsed condition. Tension applied to the tension cord 19 by the control mechanism 3 collapses the pressure compensator diaphragm 20, and pressurizes the filling media contained within it (see e.g. FIGS. 5B and 5C). This filling media volume is then transferred to the occlusive cuff 2 which inflates to occlude the urethra. The pressure generated within the pressure compensator diaphragm 20 is determined by its cross-sectional area and the force applied to the tension cord 19 according to the equation:

$$Pressure = Force/Cross\text{-}sectional\ Area$$

When tension is released from the tension cord 19, the resilience of the compressed urethral tissue forces filling media out of the occlusive cuff 2 and re-expands the pressure compensator diaphragm 20 to the position shown in FIGS. 5A and 5B.

The pressure compensator diaphragm 20 is contained within a semi-rigid compensator shell 21 which prevents surrounding bodily tissue from collapsing around and applying unintended pressure to the pressure compensator diaphragm 20. A fluid volume 22 contained within the compensator shell 21 surrounds and is separated from the filling media volume 23 contained within the pressure compensator diaphragm 20. As the pressure compensator diaphragm 20 collapses and filling media is transferred to the occlusive cuff 2, an equal volume of fluid is transferred into the compensator shell 21. This fluid transfer prevents a vacuum from forming within the compensator shell 21 which might prevent proper collapse of the pressure compensator diaphragm 20. Fluid transfer to the compensator shell 21 is facilitated by the collapse of a flexible compensator dome 24 on the outer surface of the compensator shell 21 as shown in FIGS. 5C and 5D. Expansion of the pressure compensator diaphragm 20 causes fluid transfer from the compensator shell 21 and re-expansion of the compensator dome 24 as shown in FIGS. 5A and 5B. At the time of surgical implantation, the compensator shell 21 is filled with an isotonic filling solution such as normal saline via a needle inserted into the septum 9.

The pressure compensator 4 components may all be manufactured from silicone rubber. Wear between opposing surfaces of the pressure compensator diaphragm 20 may be minimized using the low-coefficient of friction surface treatment described above for the occlusive cuff 2.

Control Mechanism

Tension applied to the pressure compensator diaphragm 20 is supplied by a control mechanism 3 implanted in the scrotum of the male or in the abdominal wall of the female or in a miniaturized version within the labia of the female. See e.g. FIGS. 6A to 7C. Depression of an activation button 25 (e.g. 5) on the control mechanism 3 through the intact skin causes a spring force to retract the pressure compensator diaphragm 20 and apply a constant pressure to the urethra 13 which it encircles. Depression of a deactivation button 26 (e.g. 6) also located on the control mechanism 3, releases the spring force from the pressure compensator diaphragm 20 and removes pressure from the urethra 13.

Embodiments of various control mechanisms are described in great detail in U.S. Pat. No. 8,007,429 B2 VESSEL OCCLUSIVE DEVICE AND METHOD FOR OCCLUDING A VESSEL. One of these embodiments is further described in below.

Pulley 27 counter-rotation is accomplished when the user depresses the deactivation button 26 exiting the control mechanism 3. A cable 28 wraps around the small pulley 29 at one end and the radiused base of the deactivation button 26 at its other end as shown in FIGS. 6A and 6B. As the deactivation button 26 advances, the distance the cable 28 is pulled, is magnified relative to the distance the deactivation button 26 is depressed.

When the deactivation button 26 is depressed to its full extent, a détente pin 30 contained within the deactivation button 26 engages a lever 31, which prevents the deactivation button 26 from returning to its original extended position as shown in FIG. 7A-7C. The lever 31 is biased by a spring 32 captured between the lever 31 and a silicone rubber boot 7 (see e.g. FIG. 1) surrounding the control mechanism 3. As the deactivation button 26 is depressed, the deactivation button dome 33 of the flexible silicone boot 7 deforms with the force applied to it, but rebounds to its original shape when the force is removed. In this way, the occlusive cuff 2 is held in a condition which does not compress the urethra. Rebounding of the deactivation button dome 33 prevents tissue capsule formation, which normally forms around implanted devices over time, restricting movement of the deactivation button 26.

When the patient desires to return to a continent state with the urethra 13 compressed, the silicone boot 7 is depressed over the lever 31 as shown in FIG. 7C. See e.g. arrow, activation button 25 in FIG. 7C. This disengages the lever 31 from the Détente pin 30, allowing the deactivation button 26 to return to an extended position under the bias of a constant force spring 34 nested within the pulley 27.

Post-Implantation Refilling/Repressurization

From clinical history with other commercially available artificial urinary sphincters (AUS), it is noted that post-implantation pressures applied to the urethra are frequently inadequate to provide improved continence. In these cases, the only recourse is for the patient to use other means to manage their incontinence, or to have the implanted AUS removed and replaced with one of a higher pressure. Increased risk of surgical mortality and morbidity exists with any additional surgical intervention.

If patients implanted with the hydraulic urethral occlusive device continue to leak urine, the device may be re-pressurized to a higher pressure to reduce this degree of leakage. Re-pressurization is performed by accessing the needle port 8 with a needle to allow fluid communication between the hydraulic urethral occlusive device interior and a syringe attached to a pressure transducer. The pressure transducer is used to confirm the pressure infused into the hydraulic urethral occlusive device interior by the syringe. Alternately, the needle may be attached to a bag of saline which may then be elevated to provide a water column pressure equivalent to the pressure desired within the hydraulic urethral occlusive device interior. This procedure may be performed multiple times until the patient achieves the desired degree of continence.

The pressure maintained in the device may be defined as Pressure=Force/Cross-sectional Area as given above. The Cross-sectional Area is the fixed value established by the pressure compensator diaphragm 20. However, the force generated by the constant force spring 34 is not perfectly constant and increases gradually with increased rotational displacement of the pulley 27 in which the constant force spring 34 is contained. The incremental fluid volume infused into the hydraulic urethral occlusive device interior during refilling/repressurization increases this rotational displacement to incrementally increase the interior pressure.

Alternative Electro-Mechanical Control Mechanism

The mechanical control mechanism 3, described above, may be replaced by a closed loop, electro-mechanical, servo-control system. This system also has occlusive cuff 2 and pressure compensator diaphragm 20 as described above, a pulley 35, rotary actuator such as a motor 36, micro-processor based control mechanism 37, power supply 38, and separate urethral 39 and abdominal 40 pressure sensing elements. In this embodiment, the rotary actuator 36 turns the pulley 35 which, in turn, takes up and applies load to the tension sutures 41 to pressurize the pressure compensator diaphragm 20 and occlusive cuff 2 to occlude the urethra 13. See e.g. FIG. 8. It is to be appreciated that a linear actuator such as a lead screw may be used in place of a rotary actuator.

In its resting state, the pulley 35 is biased so that the pressure compensator diaphragm 20 applies 0 to 20 cm $H_2O$ pressure to the urethra 13. This pressure range is adequate to prevent urinary leakage during normal, unstressful activities. Urethral pressure is continuously or intermittently monitored by a urethral pressure sensing element 39 situated between the occlusive cuff 2 and the outer surface of the urethra 13. Abdominal or bladder pressure is monitored continuously or intermittently by a pressure sensor 40 implanted within the abdominal cavity, within the abdominal wall, within the bladder or within the bladder wall.

As bladder filling occurs, bladder pressure increases within the range of 20-60. Sensing this pressure increase, the abdominal/bladder pressure sensor 40 signals the control mechanism 37 to turn the motor 36 on and cause the pulley 35 to rotate and affect a rise in urethral pressure. When the urethral pressure sensing element 39 detects that urethral pressure is 60-80 cm $H_2O$, the motor 36 is turned off and the pulley 35 held in position to prevent any further pressure increase or decrease. Once the abdominal/bladder pressure reduces to 20 cm $H_2O$ or less, the control mechanism 37 is again signaled to allow the rotary actuator 36 to reverse direction and reduce tension on the traction sutures 41 until urethral pressures between 0 and 20 cm $H_2O$ are achieved.

Stressful events such as coughing, sneezing, laughing, etc. can often cause abdominal/bladder pressures spikes in excess of 60 cm $H_2O$. Pressure rise times of 35 msec and elevated pressure durations of approximately 100 msec have been recorded. Sensing these pressure levels, the control mechanism 37 causes the rotary actuator 36 to turn on and rotate the pulley 35 to affect a rise in urethral pressure of as much as 120 cm $H_2O$. When abdominal/bladder pressure declines to 20 cm $H_2O$ or less, the control mechanism 37 allows the rotary actuator 36 to reverse direction and reduce tension on the traction sutures 41 until urethral pressures between 0 and 20 cm $H_2O$ are achieved.

When the user wishes to void urine, a switch on the control mechanism 37 is manually activated through the skin. This action causes the pulley 35 to free-wheel, reducing traction suture 41 tension until a 0 cm $H_2O$ urethral pressure is achieved. The user then voids urine through the unobstructed urethra 13. The user may then be required to manually depress the switch again to return the device to its resting mode or the device will be programmed to automatically return to its resting mode within 3-5 minutes.

While the embodiments have been described in terms of various specific embodiments, those skilled in the art will recognize that the embodiments can be practiced with modification within the spirit and scope of the claims.

What is claimed is:

1. An implantable occlusive device, comprising:
   an occlusive cuff;
   a control mechanism;
   a pressure compensator; and
   a tension cord that travels from the control mechanism to a diaphragm defining a filling media volume inside the pressure compensator, the diaphragm is configured to operate between an expanded condition and a collapsed condition,
   the control mechanism is in fluid communication with the occlusive cuff, through attachment via a flexible tube,
   the control mechanism is in fluid communication with an inner portion of the pressure compensator, through attachment via a flexible conduit,
   the control mechanism including an activation button and a deactivation button, the activation button upon depression, hydraulically inflates with hydraulic fluid the occlusive cuff to apply a preset occlusive pressure on a tubular body, the deactivation button upon depression, hydraulically evacuates the hydraulic fluid from the occlusive cuff to remove the preset occlusive pressure on the tubular body, wherein
   the control mechanism is configured to apply tension to the tension cord to collapse the diaphragm and the filling media volume into the collapsed condition, where the hydraulic fluid transfers to the occlusive cuff to inflate the occlusive cuff, and the control mechanism is configured to release tension from the tension cord to evacuate the hydraulic fluid from the occlusive cuff, where the hydraulic fluid transfers to the pressure compensator to expand the diaphragm and the filling media volume to the expanded condition.

2. The device of claim 1, wherein the occlusive cuff is adjustable to encircle a urethra.

3. The device of claim 2, wherein the occlusive cuff comprises an expandable pouch affixed to a cuff backing strip, the expandable pouch is inflatable when the hydraulic fluid enters the expandable pouch through the flexible tube so as to apply a preset urethral pressure, and the expandable pouch is deflatable when the hydraulic fluid evacuates from the expandable pouch through the flexible tube so as to remove the preset urethral pressure.

4. The device of claim 1, wherein the occlusive cuff comprises sizing detents, a free end, and a locking clip, the free end is insertable through the locking clip to lock the occlusive cuff to one of the sizing detents.

5. The device of claim 1, wherein the control mechanism is encapsulated by a silicone boot.

6. The device of claim 1, wherein the control mechanism comprises a septum.

7. The device of claim 1, wherein the pressure compensator further comprises a shell, a fluid volume contained within the shell and that surrounds and is separated from the filling media volume, as the diaphragm is collapsed, fluid transfers into the fluid volume, and as the diaphragm expands, fluid transfers out of the fluid volume.

8. The device of claim 7, wherein the pressure compensator further comprises a dome, the dome is configured to allow fluid to transfer into the fluid volume when the diaphragm collapses and allow fluid to transfer out of the fluid volume when the diaphragm expands.

9. The device of claim 7, wherein the inner portion of the pressure compensator contains a fluid different from a fluid in the fluid volume.

10. The device of claim 1, wherein the pressure compensator comprises a septum.

11. The device of claim 1, wherein the control mechanism includes an electro mechanical control.

12. The device of claim 1, wherein the control mechanism is configured to incrementally increase occlusive pressure on the tubular body.

13. A method of tubular body occlusion, comprising:
   applying a tension to a tension cord to collapse a diaphragm inside a pressure compensator shell to transfer hydraulic fluid to an occlusive cuff, the transfer of hydraulic fluid being via first and second conduits in fluid communication with a control mechanism, wherein the first conduit is connected to the control mechanism and the occlusive cuff and the second conduit is connected to the control mechanism and the pressure compensator, wherein the pressure compensator is physically separated from the control mechanism by the second conduit;
   pressurizing the occlusive cuff as a result of the transfer of hydraulic fluid from the collapsing of the diaphragm inside the pressure compensator shell;
   occluding a tubular body surrounded by the occlusive cuff as a result of pressurizing of the occlusive cuff; and
   during a desired state of non-occlusion, releasing the tension from the tension cord to depressurize the occlusive cuff to transfer the hydraulic fluid from the occlusive cuff to the inside of the pressure compensator to thereby expand the diaphragm, and during a desired state of occlusion, repressurizing the occlusive cuff, by repeating the steps of applying, pressurizing, and occluding.

14. The method of claim 13, wherein the control mechanism is a mechanical control mechanism.

15. The method of claim 13, wherein the control mechanism is an electro mechanical control mechanism.

16. The method of claim 13, further comprising incrementally increasing pressure on the tubular body.

17. An implantable occlusive device, comprising:
   an occlusive cuff;
   a control mechanism;
   a pressure compensator; and
   a tension cord that travels from the control mechanism to a diaphragm defining a filling media volume inside the pressure compensator, the diaphragm is configured to operate between an expanded condition and a collapsed condition, the control mechanism is in fluid communication with the occlusive cuff, through attachment via a flexible tube, the control mechanism is in fluid communication with an inner portion of the pressure compensator, through attachment via a flexible conduit, the control mechanism including an activation button and a deactivation button, the activation button upon depression, receives hydraulic fluid from the pressure compensator and hydraulically inflates the occlusive cuff with the hydraulic fluid to apply a preset occlusive pressure on a tubular body, the deactivation button upon depression, hydraulically evacuates the hydraulic fluid from the occlusive cuff to the control mechanism to remove the preset occlusive pressure on the tubular body and provides the hydraulic fluid from the control mechanism to the pressure compensator, wherein the control mechanism is configured to apply tension to the tension cord to collapse the diaphragm and the filling media volume into the collapsed condition, where the hydraulic fluid transfers to the occlusive cuff to inflate the occlusive cuff, and the control mechanism is configured to release tension from the tension cord to evacuate the hydraulic fluid from the occlusive cuff, where the hydraulic fluid transfers to the pressure compensator to expand the diaphragm and the filling media volume to the expanded condition.

* * * * *